United States Patent [19]

Huber

[11] Patent Number: 4,663,454

[45] Date of Patent: May 5, 1987

[54] PROCESS TO PREPARE α-CHLOROALPRAZOLAM

[75] Inventor: Joel E. Huber, Kalamazoo, Mich.

[73] Assignee: The Upjohn Company, Kalamazoo, Mich.

[21] Appl. No.: 723,993

[22] Filed: Apr. 17, 1985

[51] Int. Cl.$^4$ ........................................... C07D 487/04
[52] U.S. Cl. .................................................. 540/563
[58] Field of Search ...................... 260/245.5; 540/563

[56] References Cited

U.S. PATENT DOCUMENTS 4,141,902  2/1979  Hester ................................. 260/308
4,235,775  11/1980  Meguro ............................ 260/243.3
4,250,094  2/1981  Hester .............................. 260/245.5

OTHER PUBLICATIONS

J. Med. Chem. 23, 392 (1980) J. B. Hester et al. "1-(Aminoalkyl)-6-Aryl-4H-s-Triazolo[4,3-a]benzodiazepines with Antianxiety and Antidepressant Activity".

Primary Examiner—Richard L. Raymond
Attorney, Agent, or Firm—Bruce Stein

[57] ABSTRACT

α-Halomethylbenzodiazepines (II) are produced by direct halogenation of methylbenzodiazepines (I) using sulfuryl halide.

13 Claims, No Drawings

PROCESS TO PREPARE α-CHLOROALPRAZOLAM

BACKGROUND OF THE INVENTION

α-Chloroalprazolam and α-chlorotriazolam are known, see U.S. Pat. No. 4,250,094 (Preparation 2) and No. 4,141,902 (Example 7), respectively. U.S. Pat. No. 4,141,902 also generically discloses α-bromoalprazolam and α-bromotriazolam.

Adinazolam and the 6-(o-chlorophenyl) analog of adinazolam are known, see U.S. Pat. No. 4,250,094, Examples 1 and 2, respectively.

The transformation of α-chloroalprazolam to adinazolam is known, see U.S. Pat. No. 4,250,094, Example 1. The aminolysis of α-bromoalprazolam and α-bromotriazolam is also generically known.

Various processes are known for the preparation of α-chloroalprazolam, none of which are direct chlorination of the triazolo methyl group, see, for example, U.S. Pat. Nos. 4,235,775, 4,141,902 (Example 1), 4,250,094, and J. Med. Chem., 23, 392 (1980).

The process of the present invention involves direct halogenation of the triazolo methyl group of alprazolam to produce α-chloroalprazolam or α-bromoalprazolam.

SUMMARY OF THE INVENTION

A process for preparing an α-halomethylbenzodiazepine (II) which comprises contacting a methylbenzodiazepine (I) with sulfuryl halide or a halogenating agent in the presence of an acid scavenger.

DETAILED DESCRIPTION OF THE INVENTION

The methylbenzodiazepines (I), alprazolam ($R_1$ is a hydrogen atom), and triazolam ($R_1$ is a chlorine atom) are known, see U.S. Pat. No. 3,987,052, Examples 1 and 14, respectively.

The direct halogenation of the triazolo methyl group of the methylbenzodiazepines (I) to produce α-halomethylbenzodiazepines (II) is performed by contacting the methylbenzodiazepines (I) with the appropriate sulfuryl halide or a sulfuryl halide generating agent in the presence of an acid scavenger and solvent if the acid scavenger is not also the solvent. While sulfuryl halide is operable, the sulfuryl halide may be prepared in situ by use of chlorine or bromine and sulfur dioxide. Any agents which do not react with the methylbenzodiazepines (I) and which generate either sulfuryl halide or a halogenating agent in situ which directly halogenates the methyl group are deemed equivalent to sulfuryl halide for purposes of this patent. It is preferred that the sulfuryl halide be sulfuryl chloride.

Acid scavengers are any agent which will serve to pick up the displaced proton from the methylbenzodiazepine (I) starting material and includes, for example, pyridine, poly(4-vinylpyridine), triethylamine, tetramethylurea, powdered potassium carbonate, epichlorohydrin, DMF and compounds of formula (V), see Chart B. The preferred acid scavengers are DMF and epichlorohydrin, more preferred is DMF. When DMF is the acid scavenger, it also serves as the solvent or cosolvent. Diisopropylethyl amine works poorly.

Suitable solvents are aprotic organic solvents. Preferred solvents are selected from the group consisting of THF, DMF, methylene chloride, chloroform and carbon tetrachloride and mixtures thereof. The preferred solvent is methylene chloride. Toluene is a poor solvent.

Various mixtures of acid scavengers and solvents are also operable.

The reaction can be performed in the presence of a catalyst of the formula R—CO—M (IV). It is preferred that no catalyst be used.

The reaction is performed in a temperature range of about $-60°$ to about $25°$, preferably about $-40°$ to about $-10°$.

The sulfuryl halide is added to the methylbenzodiazepine (I) slowly over a period of about 15 minutes to about 5 hours, preferably about 1 to about 4 hours. When complete, the reaction is quenched with a quenching agent such as water, saline, as is well known to those skilled in the art.

The α-halomethylbenzodiazepine (II) can be isolated by means well known to those skilled in the art (Example 4). If the α-halomethylbenzodiazepine (II) is isolated, there are various aminolysis methods well known to those skilled in the art for the conversion of the α-halomethylbenzodiazepine (II) to the therapeutically useful dimethylaminomethylbenzodiazepine (III), see U.S. Pat. No. 4,250,094. Alternatively, and preferably the α-halomethylbenzodiazepine (II) is not isolated but rather the reaction mixture can be neutralized with a base and the aminolysis subsequently performed on the crude α-halomethylbenzodiazepine (II) transforming the α-halomethylbenzodiazepine (II) intermediate into the therapeutically useful dimethylaminomethylbenzodiazepine (III), see Example 2.

The dimethylaminomethylbenzodiazepine (III) is preferably recovered by extracting the aqueous reaction mixture with methylene chloride and then replacing the lower boiling methylene chloride with toluene by distillation. Alternatively, though less preferably the aqueous reaction mixture can be extracted with toluene (Example 2).

The therapeutically useful dimethylaminomethylbenzodiazepines (III) adinazolam ($R_1$ is a hydrogen atom) and o-chloroadinazolam ($R_1$ is a chlorine atom) are known, see U.S. Pat. No. 4,250,094.

DEFINITIONS

The definitions and explanations below are for the terms as used throughout the entire patent application including both the specification and the claims.

All temperatures are in degrees Centigrade.

TLC refers to thin-layer chromatography.

THF refers to tetrahydrofuran.

DMF refers to dimethylformamide.

LC refers to high performance liquid chromatography.

When solvent pairs are used, the ratios of solvents used are volume/volume (v/v).

Alprazolam refers to 8-chloro-1-methyl-6-phenyl-4H-s-triazolo-[4,3-a][1,4]benzodiazepine.

α-Chloroalprazolam refers to 8-chloro-1-(chloromethyl)-6-phenyl-4H-s-triazolo[4,3-a][1,4]benzodiazepine.

Adinazolam refers to 8-chloro-1-[(dimethylamino)methyl]-6-phenyl-4H-s-triazolo[4,3-a][1,4]benzodiazepine.

Triazolam refers to 8-chloro-6-(o-chlorophenyl)-1-methyl-4H-s-triazolo[4,3-a][1,4]benzodiazepine.

α-Chlorotriazolam refers to 8-chloro-1-(chloromethyl)-6-(o-chlorophenyl)-4H-s-triazolo[4,3-a][1,4]benzodiazepine.

α-Bromoalprazolam refers to 1-(bromomethyl)-8-chloro-6-phenyl-4H-s-triazolo[4,3-a][1,4]benzodiazepine.

α-Bromotriazolam refers to 1-(bromomethyl)-8-chloro-6-(o-chlorophenyl)-4H-s-triazolo[4,3-a][1,4]benzodiazepine.

M is a chlorine or bromine atom.

R is alkyl of one through 4 carbon atoms or phenyl.

$R_1$ is a hydrogen or chlorine atom.

$R_2$ is a hydrogen atom, alkyl of 1 through 18 carbon atoms, cycloalkyl of 5 through 7 carbon atoms, phenyl or phenyl substituted with 1 through 3 substituents selected from the group consisting of alkyl of 1 through 3 carbon atoms; a fluorine, chlorine, or bromine atom, or alkoxy where the alkyl portion is from 1 through 3 carbon atoms; when $R_2$ is alkyl it can be cyclized with either $R_3$ or $R_4$ to form a ring of 5 through 7 atoms.

$R_3$ and $R_4$ are the same or different and are alkyl of 1 through 8 carbon atoms or phenyl; when $R_3$ and $R_4$ are both alkyl they can be cyclized to form a ring of 5 through 7 atoms.

X is a chlorine or bromine atom.

EXAMPLES

Without further elaboration, it is believed that one skilled in the art can, using the preceding description, practice the present invention to its fullest extent. The following detailed examples describe how to prepare the various compounds and/or perform the various processes of the invention and are to be construed as merely illustrative, and not limitations of the preceding disclosure in any way whatsoever. Those skilled in the art will promptly recognize appropriate variations from the procedures both as to reactants and as to reaction conditions and techniques.

EXAMPLE 1

α-Chloroalprazolam (II)

Acetyl chloride (356 μl) is added to a solution of alprazolam (I, U.S. Pat. No. 3,987,052, 9.264 g) in DMF (15 ml) and methylene chloride (40 ml) at −30°. Sulfuryl chloride in methylene chloride (3.0M, 13 ml) is then immediately added dropwise over 4.25 hr at −21° to −19°. The mixture is stirred for 15 minutes at which time LC indicates less than 1% remaining alprazolam and greater than 95% desired (II). The reaction is quenched at −10° with water (10 ml), added carefully at first because of the exotherm, and then the pH is adjusted from 1.4 to 11.4 with the slow addition of sodium hydroxide (50%, 10 ml). The α-chloroalprazolam (II) is not isolated but rather subjected to aminolysis according to Example 2.

EXAMPLE 2

Adinazolam (III)

An aqueous dimethylamine solution (5.4M, 10.0 ml) is added at 20° to α-chloroalprazolam (Example 1) and the two-phase mixture is complete after 1 hr. The reaction mixture is added to toluene (150 ml). The layers are separated and the aqueous layer is washed with toluene (25 ml) and then discarded. The organic layers are washed sequentially with water (3×50 ml), combined, filtered through a cotton wad and concentrated to give crude adinazolam.

The crude adinazolam is taken up in hot toluene. Solids form rapidly after standing at 0° for 45 min. The solids are filtered, washed with cold toluene (2×3 ml) and dried under vacuum at 50° overnight to give the title compound. Additional adinazolam can be obtained from the filtrate.

EXAMPLE 3

Adinazolam mesylate

Adinazolam (4.0 g) is dissolved in methanol (15 ml) and n-butyl acetate (55 ml) and filtered. Methane sulfonic acid (1.038 g) in n-butyl acetate (5 ml) is added with filtration. A 5 ml rinse of n-butyl acetate is used. The mixture is heated to 110° over 30 minutes while the methanol is removed by distillation under a slight vacuum. The slurry becomes more stirrable after 45 minutes at 110°–112°. The slurry is maintained at this temperature for 1 hr during which about 5 ml of n-butyl acetate is removed by distillation. The slurry is cooled to −10° for 30 minutes and the solids collected by filtration, washed with cold n-butyl acetate (2×5 ml) and dried under vacuum at 55° overnight to give the title compound.

EXAMPLE 4

α-Chloroalprazolam (II)

A solution containing sulfur dioxide (6.4 mmol) and DMF (9.6 mmol) in methylene chloride is added to a mixture of alprazolam (2 mmol) in DMF (2 ml) and methylene chloride (10 ml) at −20°. Chlorine (about 2.1 mmol) is bubbled in over a 2 min period at −20°. After about 2 hrs additional chlorine (1 mmol) is introduced. After 2 hrs the reaction is quenched with methanol (10 ml) and then added to toluene (50 ml) and water (100 ml). The phases are separated and the organic layer is washed thoroughly with water, dried and concentrated. The higher boiling residue is crystallized from acetone (8 ml) and hexane (15 ml) at 20°–25°. The product is collected by vacuum filtration, washed with acetone/hexane (½, 5 ml) and dried to provide the title compound, mp 181° with decomposition.

EXAMPLE 5

Adinazolam (III)

A mixture of alprazolam (37.05 g) dissolved in methylene chloride (160 ml) and DMF (60 ml) is cooled to −20°. Sulfuryl chloride in methylene chloride (3.0M, 52 ml) is added dropwise. The addition proceeds for 3.5 hrs (15 ml/hr). The reaction contents are then stirred for another hour.

In a separate flask water (100 ml), sodium hydroxide (50%, 40 ml) and aqueous dimethylamine (26%, 40 ml) are mixed. The amine solution is cooled to −5° and the α-chloroalprazolam mixture is added slowly to the water/sodium hydroxide/dimethylamine mixture such that the temperature does not rise above 5°. This takes approximately 5–8 min. This two-phase mixture is then stirred overnight at 5°.

The reaction mixture is then distilled at one atmosphere and 40° until approximately 80% of the methylene chloride is removed (130 ml) distillate. At this time toluene (100 ml) is added and the reaction mixture stirred well. The phases are then permitted to separate. The aqueous phase is decanted and back-extracted with toluene (25 ml). The aqueous phase is then discarded. The toluene (25 ml) is added back to the reaction mixture and this mixture is washed with water (3×100 ml) at 50°. The warm water is required for rapid phase separation. The aqueous washes are combined and back-extracted with toluene (50 ml) at 50°. The aqueous phase is discarded and the toluene combined with the reaction mixture for a total volume of about 175 mls. The toluene is then removed by distillation at one atmosphere and 110° until 135 ml has been removed and about 40 ml remains. The heating is discontinued and isooctane (40 mls) is added to the mixture. Crystals form immediately and the mixture is permitted to cool slowly to 20°-25° and then continued to cool to −20° and held at −20° with slow stirring for an additional hour. The crystals are obtained by filtration, washed with a mixture of cold (−20°) toluene/isooctane, 50/50, (10 ml). The crystals are dried under vacuum at 60° overnight to give the title compound.

EXAMPLE 6

α-Bromoalprazolam (II)

Sulfur dioxide (1.35 equivalents) in a DMF-methylene chloride solution is added to a mixture of alprazolam (I, 618 mg) in DMF (1.0 ml) and methylene chloride (15 ml) at −10°. Bromine (258 μl) in methylene chloride (6 ml) is added dropwise over a 2 hr period while the temperature is maintained at −10° to −2°. The reaction is stirred for another 1.75 hr at −5°. TLC (silica gel, acetone/methylene chloride: 40/60, UV detection) indicates about 90% product and about 10% starting material. The mixture is added to toluene (100 ml). The organic layer is washed dilute sodium bicarbonate (50 ml), dilute sodium sulfite solution (50 ml) and water (2×50 ml). The organic layer is filtered through cotton and then concentrated to constant weight to give the title compound, which is purified by mplc and then crystallized from ethyl acetate, mp=256° with decomposition.

EXAMPLE 7

Adinazolam (III)

Following the general procedure of Example 2 and making non-critical variations but starting with α-bromoalprazolam (II, Example 6), the title compound is obtained.

CHART A

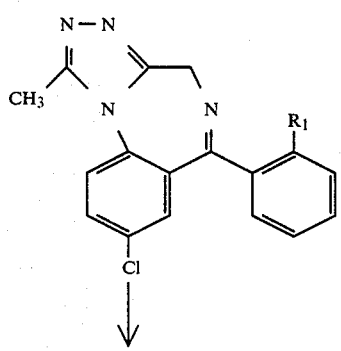

-continued
CHART A

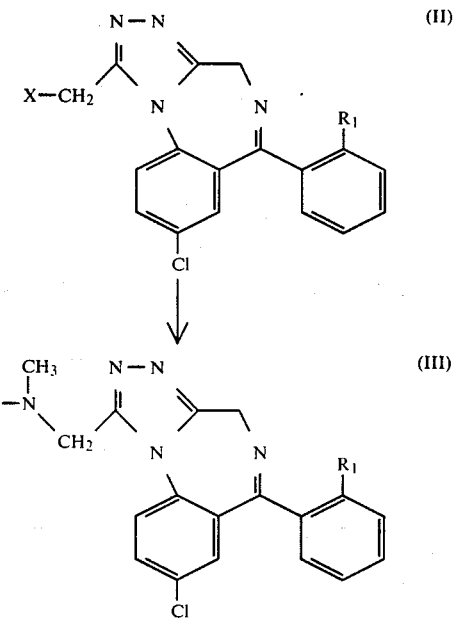

CHART B

I claim:
1. A process for preparing an α-halomethylbenzodiazepine of the formula

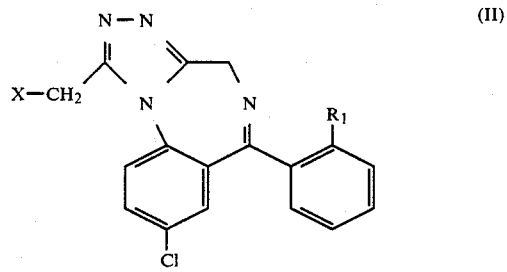

which comprises contacting a methylbenzodiazepine of the formula

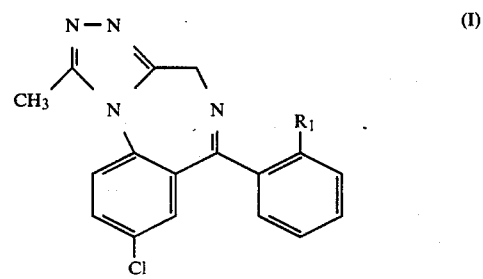

with sulfuryl halide in the presence of an acid scavenger where $R_1$ is a hydrogen or chlorine atom;

X is a chlorine or bromine atom.

2. A process according to claim 1 where the process is performed in an aprotic organic solvent.

3. A process according to claim 2 where the process is performed in a solvent selected from the group consisting of methylene chloride, DMF, THF, chloroform or carbon tetrachloride and mixtures thereof.

4. A process according to claim 1 where the process is performed in the temperature range of about −60° to about 25°.

5. A process according to claim 4 where the temperature range is about −40° to about −10°.

6. A process according to claim 1 where the methylbenzodiazepine is alprazolam.

7. A process according to claim 1 where the methylbenzodiazepine is triazolam.

8. A process according to claim 1 where the reaction is performed in the absence of a catalyst of the formula R—CO—M (IV) where R is alkyl of 1 through 4 carbon atoms or phenyl and where M is a chlorine or bromine atom.

9. A process according to claim 1 where the acid scavenger is pyridine, poly(4-vinylpyridine), triethylamine, tetramethylurea, powdered potassium carbonate, epichlorohydrin or a compound of the formula

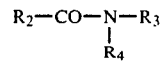

where $R_2$ is a hydrogen atom, alkyl of 1 through 18 carbon atoms, cycloalkyl of 5 through 7 carbon atoms, phenyl or phenyl substituted with 1 through 3 substituents selected from the group consisting of alkyl of 1 through 3 carbon atoms; a fluorine, chlorine, or bromine atom, or alkoxy where the alkyl portion is from 1 through 3 carbon atoms; when $R_2$ is alkyl it can be cyclized with either $R_3$ or $R_4$ to form a ring of 5 through 7 atoms, $R_3$ and $R_4$ are the same or different and are alkyl of 1 through 8 carbon atoms or phenyl; when $R_3$ and $R_4$ are both alkyl they can be cyclized to form a ring of 5 through 7 atoms.

10. A process according to claim 9 where the acid scavenger is a DMF or epichlorohydrin.

11. A process according to claim 10 where the acid scavenger is DMF.

12. A process according to claim 1 where X is a chlorine atom.

13. A process according to claim 1 where the sulfuryl halide is produced in situ by reaction of sulfur dioxide and chlorine or bromine.

* * * * *